United States Patent [19]

Ramachandran et al.

[11] Patent Number: 4,536,315

[45] Date of Patent: Aug. 20, 1985

[54] PERFUME-CONTAINING CARRIER HAVING SURFACE-MODIFIED PARTICLES FOR LAUNDRY COMPOSITION

[75] Inventors: Pallassanna Ramachandran, Robbinsville; Paul S. Grand, Highland Park, both of N.J.

[73] Assignee: Colgate Palmolive Co., New York, N.Y.

[21] Appl. No.: 499,927

[22] Filed: Jun. 1, 1983

[51] Int. Cl.[3] ........................ C11D 17/06; C11D 1/38; C11D 9/44; A61K 7/46

[52] U.S. Cl. ................................ 252/174.11; 252/8.8; 252/174.25; 252/522 A; 252/528; 252/547

[58] Field of Search ...................... 252/174.11, 174.25, 252/522 A, 8.8, 528, 547

[56] References Cited

U.S. PATENT DOCUMENTS

| | | | |
|---|---|---|---|
| 3,256,180 | 6/1966 | Weiss | 252/8.8 R |
| 3,862,058 | 1/1975 | Nirschl et al. | 252/8.6 X |
| 3,886,075 | 5/1975 | Bernardino | 252/8.8 X |
| 3,993,573 | 11/1976 | Gloss | 252/89.1 X |
| 4,326,967 | 4/1982 | Melville | 252/8.8 |
| 4,339,356 | 7/1982 | Whyte | 252/174.11 X |
| 4,499,012 | 2/1985 | Farrell | 252/522 A |

FOREIGN PATENT DOCUMENTS

| | | | |
|---|---|---|---|
| 0036720 | 9/1981 | European Pat. Off. | 252/522 A |
| 0069840 | 6/1978 | Japan | 252/522 A |

OTHER PUBLICATIONS

"Formation and Properties of Clay-Polymer Complexes" by B. K. G. Theng., Elsevier Scientific Publishing Company, New York, pp. 37-39, 82-87 and 95, (1979).

*Primary Examiner*—John E. Kittle
*Assistant Examiner*—Mukund J. Shah
*Attorney, Agent, or Firm*—Bernard Lieberman; Murray M. Grill; Herbert S. Sylvester

[57] ABSTRACT

A perfume-containing carrier is provided for use in admixture with a particulate laundry detergent composition or as an additive to the wash solution separate from the detergent composition to impart a pleasing fragrance to laundered fabrics. The perfume-containing carrier comprises (i) discrete particles containing at least 75%, by weight, of a clay mineral other than talc and/or a zeolite; (ii) a perfume, said perfume being absorbed and/or absorbed on said particles; and (iii) a fabric-adhesive agent comprising at least one of an anionic detergent compound, a nonionic detergent compound, or a cationic compound selected from the group consisting of primary, secondary and tertiary amines and their water-soluble salts, diamine and diammonium salts, and quaternary ammonium, phosphonium and sulfonium compounds, said fabric-adhesive agent being in contact with said particles and forming at least a partial coating upon the surface thereof, the perfume-containing carrier containing less than about 5%, by weight, of surface active detergent compounds other than cationic detergents.

28 Claims, No Drawings

PERFUME-CONTAINING CARRIER HAVING SURFACE-MODIFIED PARTICLES FOR LAUNDRY COMPOSITION

CROSS REFERENCE TO RELATED APPLICATION

This application is related to copending U.S. Application Ser. No. 3875 (A) filed on even date herewith, which describes a perfume-containing carrier comprising discrete particles containing a clay mineral other than talc and/or a zeolite; and a perfume.

BACKGROUND OF THE INVENTION

This invention relates to perfume-containing carriers which significantly enhance the substantivity of perfume to laundered fabrics. More particularly, this invention relates to particulate detergent compositions which include as a component thereof a perfume-containing carrier which is able to impart a pleasing perfume fragrance to the finished laundered fabrics with only minimal amounts of perfume.

Perfume substances which modify or enhance the aroma of detergent compositions or impart a pleasing aroma thereto are well-known in the art. U.S. Pat. No. 4,131,555 and 4,228,026, are illustrative of patents which describe substances intended to impart a pleasing aroma or fragrance to liquid and granular detergent compositions. The described methods of preparation consist of mixing the perfume substances, in solid form, with the prepared detergent compositions to form a homogeneous composition. Perfumes which are in liquid form are conventionally added to liquid detergent compositions as a component thereof or sprayed upon the surface of granular detergent compositions. However, detergent compositions which are thus prepared are unable to impart a perfume fragrance to the fabrics being laundered notwithstanding the enhanced aroma of the composition itself. Primarily, this is because the perfume substances in the detergent composition are rapidly dispersed and diluted during laundering in the aqueous wash solution along with the water-soluble components of the detergent composition. Consequently, only a relatively minor amount of the perfume is available to contact and adhere to the fabric being laundered, the major portion of the perfume being drained from the washing machine with the wash solution during the wash cycle. Moreover, to the extent that some perfume is still in contact with the fabric after the washing operation, it tends to be dissipated subsequently during drying, such as, for example, in a gas or electric dryer in which the washed fabrics are tumbled at relatively high temperatures. As a result, fabrics laundered with conventional detergent compositions generally retain only a very faint perfume fragrance which has no particular aesthetic appeal to the user. There is, therefore, a need in the art for an additive to conventional detergent compositions which can effectively provide a perfume fragrance to fabrics being laundered such that the finished laundered fabrics have added appeal to the user.

U.S. Pat. No. 4,259,373 discloses a fabric conditioning article for use in an automatic washer or dryer consisting of a sealed water-in-soluble pouch containing what is described as a softener/antistat composition. In Example II of the patent, there is described a preparation procedure for such antistat composition wherein clay and solid perfume are mixed and the mixture then blended with sprayed particles of certain quaternary ammonium salts. The resulting composition is then filled into a sealed polyester pouch.

Included among the perfume-containing carriers of the invention described herein is a particular embodiment which comprises a perfume, particles of clay and a quaternary ammonium compound (sometimes referred to herein as a "QA" compound for convenience). Compositions containing clay and QA compounds are broadly described in the art relating to fabric softeners and anti-stat compositions. U.S. Pat. No. 3,886,075, for example, describes a composition containing a smectite clay, a water-soluble QA compound and an "amino compatabilizing agent" which is said to provide fabric softening and anti-static effects. U.S. Published Patent Application No. B305,417 describes a granular laundering composition comprising a soap-based granule, a smectite-type clay and a quaternary ammonium anti-static agent. In U.S. Pat. No. 3,862,058, a clay and a quaternary ammonium compound are added to a non-soap synthetic detergent compound to provide a granular laundry detergent composition. U.S. Pat. Nos. 3,993,573 and 3,954,632 describe fabric softening compositions containing the aforementioned clay and QA compounds in combination with a so-called "acid compatibilizing agent". U.S. Pat. No. 4,292,035 discloses a softening composition comprising smectite clay; an amine or quaternary ammonium compound as a softening agent; and an anionic surfactant wherein the fabric softening agent is reacted with the clay to form an "organo-clay complex" prior to the addition of the anionic surfactant.

The methods described in the art for preparing the aforementioned fabric softening compositions are characterized by either a deposition of QA compound upon granules composed of a uniform blend of clay with detergent and other ingredients (rather than a preferential deposition upon clay granules) or alternatively, the QA compound is reacted with the clay to provide a modified clay in which preferably from about 10 to about 60 molar percent of the exchangeable cations are alkyl substituted ammonium ions. Thus, for example, U.S. Pat. Nos. 3,862,058 and 3,886,075 describe a method of preparation whereby the clay is initially admixed in a crutcher with the detergent, builder and other ingredients of the laundering composition and the resulting mixture then spray-dried to form granules. The QA compound is thereafter sprayed upon the granules from a melt, it being a critical aspect of the method of preparation to avoid spraying the detergent granules with an aqueous solution or suspension of the QA compound. United States Published Patent Application B305,417 discloses a method of preparation wherein clay is mixed with soap-based granules in a drum mixer. The QA compound is then added to the resulting composition by spraying from a melt. U.S. Pat. No. 3,594,212 describes a method of softening fibrous materials wherein such materials are successively impregnated with an aqueous dispersion of clay and an aqueous solution of QA compound, the amount of QA compound in solution being sufficient to effect at least a partial cation exchange with the clay retained on the fibrous material. In U.S. Pat. No. 3,948,790 to Speakman, there is described a procedure for preparing "quaternary ammonium clays" whereby a QA compound is reacted with clay by slurrying the untreated clay in a solution containing the desired quantity of QA compound. The QA compounds which may be thus employed are said to be restricted to short-chain compounds having a maximum of four carbon atoms per chain, the total number of carbon atoms in the compound not exceeding eight. The quantity of such QA compound added to the solution is controlled so as to provide the desired degree of ion exchange with the clay. The examples of the patent describe various treated clays in which from about 5 to 40% of the exchangeable cations are replaced by quaternary ammonium cations, the amount of QA compound in solution being necessarily restricted to that which is required to effect a partial exchange reaction with the clay. Accordingly, the prior art does not contemplate the particular combination of clay particle and QA compound employed in the present invention, much less contemplate using such combination as a carrier for perfume in accordance with the invention.

SUMMARY OF THE INVENTION

The present invention provides an improved perfume-containing carrier comprising: (i) discrete particles containing at least 75%, by weight, of a clay mineral other than talc and/or a zeolite; (ii) a perfume, said perfume being adsorbed and/or absorbed on said particles; and (iii) a fabric-adhesive agent comprising at least one of an anionic detergent compound, a nonionic detergent compound, or a cationic compound selected from the group consisting of primary, secondary and tertiary amines and their water-soluble salts, diamine and diammonium salts, and quaternary ammonium, phosphonium and sulfonium compounds, said fabric-adhesive agent being in contact with said particles and forming at least a partial coating upon the surface thereof, the perfume-containing carrier containing less than about 5%, by weight, of detergent compounds other than cationic detergents.

In accordance with the process aspect of the invention, the deposition of perfume or laundered fabrics is effected by contacting the stained and/or soiled materials to be laundered with an aqueous solution or dispersion which contains the above-defined perfume-containing carriers.

The term "perfume" as used herein refers to odoriferous materials which are able to provide a pleasing fragrance to fabrics, and encompasses conventional materials commonly used in detergent compositions to counteract a malodor in such compositions and/or provide a pleasing fragrance thereto. The perfumes are preferably in the liquid state at ambient temperature, although solid perfumes are also useful. Included among the perfumes contemplated for use herein are materials such as aldehydes, ketones, esters and the like which are conventionally employed to impart a pleasing fragrance to liquid and granular detergent compositions. Naturally occuring plant and animal oils are also commonly used as components of perfumes. Accordingly, the perfumes useful for the present invention may have relatively simple compositions or may comprise complex mixtures of natural and synthetic chemical components, all of which are intended to provide a pleasant odor or fragrance when applied to fabrics. The perfumes used in detergent compositions are generally selected to meet normal requirements of odor, stability, price and commercial availability. A description of the materials conventionally used in detergent perfumery is set forth by R. T. Steltenkamp, *The Journal of The American Oil Chemists Society,* Vol. 45, No. 6, pp. 429–432, such disclosure being incorporated herein by reference.

The term "particles" as used throughout the specification and claims with regard to the perfume-containing carrier is intended to encompass a wide variety of particulate matter of differing shape, chemical composition, particle size and physical characteristics, the essential common characteristic being that such particles contain at least 75%, by weight, of a clay mineral and/or a zeolite. The particles are desirably free-flowing in nature. The "weight percent" of the clay material and the zeolite refers to the weight of such materials including the water and impurities associated with the particular clay or zeolite employed. Accordingly, the carrier particles may be in the form of finely divided powders, as well as relatively larger-sized granules, beads or agglomerated particles, and may be produced by diverse methods of manufacture such as spray-drying, dry-blending or agglomeration of individual components. Particularly preferred carrier particles for use herein are dentonite agglomerates produced by the method described in USSN 366,587, filed Apr. 8, 1982, the disclosure of which is incorporated herein by reference. The carrier particles may thus optionally include in addition to the clay mineral and/or zeolite, materials which are compatible with conventional laundering compositions, examples of suitable materials including binding or agglomerating agents, e.g., sodium silicate, dispersing agents, detergent builder salts, filler salts as well as common minor ingredients present in conventional laundry detergent compositions such as dyes, optical brighteners, anti-redeposition agents and the like. For purposes of the invention, the particles should contain less than about 5%, by weight, of surface active detergent compounds other than cationic detergent compounds, the latter being intended for use in the present carriers in amounts up to about 16%, by weight of the carrier as a fabric-adhesive agent.

The term "discrete" as used herein with regard to the particles refers to the fact that such particles are employed in the present invention as individually distinct particles, thus excluding, for example, carrier particles which are encompassed within a matrix of other materials, or which are blended with other ingredients such that the particles become a component of a larger aggregate material rather than being in the form of individual and distinct particles.

The present invention is characterized by an effective perfume-containing carrier wherein the carrier particles contain at least 75%, by weight, preferably at least 90%, by weight, of a clay material other than talc and/or a zeolite. The major portion of the perfume associated with the carrier, preferably at least 95% thereof, is adsorbed and/or absorbed on said particles, the terms "adsorbed" and "absorbed" being used herein to refer to the physical association of the perfume with the carrier particles. Unlike conventional practice wherein the perfumes added to granular detergent compositions are sprayed upon or otherwise contacted with the water-soluble spray-dried granular powders, the perfumes employed in the present invention are contacted with particles of a clay mineral or zeolite which are, for the most part, water-insoluble. It has been found that the perfume thus associated with the carrier particles remains primarily concentrated upon such particles during laundering rather than being dispersed in the aqueous wash solution. This provides a significant advantage during laundering insofar as the perfume-containing carrier particles in the wash solution are likely to contact the laundered fabrics and be dispersed thereupon, particularly in a washing machine where the wash solution is mechanically drained through the fabric during the wash cycle. The perfume is thus maintained proximate to the finished laundered fabric, preventing the dissipation of the perfume fragrance from such fabrics.

Moreover, retention of the carrier particles upon the surface of the laundered fabrics is enhanced by the fabric adhesive agent which forms at least a partial coating upon the surface of the particles. Thus, for example, the use of an anionic or nonionic surfactant as a fabric adhesive agent in accordance with the invention provides a pasty adhesive-like surface to the carrier particles, increasing the likelihood of such particles being entrapped upon the fabrics during laundering. The use of a cationic compound similarly enhances fabric adhesion, albeit in a different manner. Although applicants do not wish to be bound to a particular theory of operation, it is believed that the deposition of a cationic compound upon the surface of the particles imparts a positive surface charge to such particles which creates a driving force for the positively charged particles to attach themselves to the negatively charged surface of the fabrics being laundered, and particularly, to fabrics containing substantial amounts of cotton. Furthermore, the surface modified particles of clay or zeolite are generally hydrophobic in nature, in clay itself being hydrophilic. The hydrophobicity of the particles is particularly advantageous in hand-wash laundering operations because the hydrophobic particles are not as readily dispersable in the aqueous hand-wash solution as untreated particles and, therefore, tend to remain upon the surface of the wash solution for longer periods of time. This has the effect of enhancing the availability of such particles for contact with and deposition upon the fabrics being laundered, thereby increasing the likelihood of maintaining the desired perfume fragrance in the hand-washed fabrics.

DETAILED DESCRIPTION OF THE INVENTION

The perfume-containing carriers of the invention are comprised of three essential ingredients: a clay mineral and/or a zeolite; a perfume; and a defined fabric-adhesive agent. The weight ratio of clay mineral or zeolite to perfume in the carriers is generally from about 10:1 to about 200:1 and preferably from about 20:1 to about 100:1. The weight of perfume in the carrier will generally vary within the range of from about 0.2 to 10%, and preferably from about 0.5 to 5%, by weight, thereof. The carriers may be conveniently employed during home laundering as additives to a laundry washing bath separate from the detergent composition, such as, for example, as a rinse-cycle additive or alternatively, the carriers may be incorporated into a conventional laundry detergent composition as a component thereof. Such fully-formulated detergent compositions generally comprise (a) from about 0.1 to about 50%, by weight, preferably from about 5 to about 30%, by weight, of said perfume-containing carrier; and (b) from 2 to about 50%, by weight, preferably from about 5 to about 40%, by weight, and most preferably from about 5 to about 30%, of one or more surface active agents selected from the group of anionic, nonionic, cationic, ampholytic and zwitterionic detergents, the amount of such detergents being additional to any detergent compound in the perfume-containing carrier. The detergent compositions optionally also contain from about 0 to about 70%, by weight, of a detergent builder salt, a concentration of from about 5% to about 50% being particularly preferred. The balance of the composition will predominantly comprise water, filler salts, such as, sodium sulfate, and optionally minor components such as binders, optical brighteners, pigments, dyes and the like which are conventional adjunct materials in detergent formulations.

For purposes of economy it is preferred that the major portion, and in most instances, preferably substantially all, of the perfume contained in the detergent composition be provided by the carriers. However, the detergent compositions useful herein may also include perfumes additional to that employed in conjunction with the above-described carriers to provide a pleasant odor to the wash solution or to the composition itself. The use of additional perfumes may also be advantageous in instances where it is used in conjunction with a limited amount of a more expensive perfume. Thus, for example, it may be economically desirable to utilize a minor amount of a relatively expensive perfume with the carrier of the invention and provide relatively larger amounts of a less expensive perfume to the granular detergent composition as a supplementary fragrance, the latter perfume being added by techniques known in the art, such as, by spraying the granular detergent powder.

The clay minerals which are generally useful herein include a wide variety of materials included among which are smectite-type clays; kaolinite, metakaolin; and attapulgite. Of the above-mentioned types of clay minerals, the smectite-type clays are preferred because they advantageously provide desirable softening effects to the laundered fabrics in addition to serving as a carrier for perfume in accordance with the invention. A detailed description of the various types of clay minerals, all of which may be used in the present invention with the exception of talc is set forth in B. K. C. Theng, *The Chemistry of Clay Organic Reactions,* John Wiley & Sons, (1974) pp. 1-15, such disclosure being incorporated herein by reference.

The crystalline types of zeolite which may be employed herein include those described in "Zeolite Molecular Series" by Donald W. Breck, published in 1974 by John Wiley & Sons, typical commercially available zeolites being listed in Table 9.6 at pages 747-749 of the text, such table being incorporated herein by reference. Zeolite structures of type A are especially desirable and are extensively described in the art; see, for example, page 133 of the aforementioned Breck text as well as U.S. Pat. No. 2,882,243. Type 4A zeolite is advantageously employed, the univalent cation of such zeolite being sodium and the pore size of the zeolite being about 4 Angstroms.

The aforementioned smectite-type clays are three-layer clays characterized by the ability of the layered structure to increase its volume several-fold by swelling or expanding when in the presence of water to form a thixotropic gelatinous substance. There are two classes of smectite-type clays: in the first class, aluminum oxide is present in the silicate crystal lattice; in the second class, magnesium oxide is present in the silicate crystal lattice. Atom substitution by iron, magnesium, sodium, potassium, calcium and the like can occur within the crystal lattice of the smectite clays. It is customary to distinguish between clays on the basis of their predominant cation. For example, a sodium clay is one in which the cation is predominantly sodium. With regard to the present carriers, aluminum silicates wherein sodium is the predominant cation are preferred, such as, for example, bentonite clays. Among the bentonite clays, those from Wyoming (generally referred to as western or Wyoming bentonite) are especially preferred.

Preferred swelling bentonites are sold under the trademark Mineral Colloid, as industrial bentonites, by Benton Clay Company, an affiliate of Georgia Kaolin Co. These materials which are the same as those formerly sold under the trademark THIXO-JEL, are selectively mined and beneficiated bentonites, and those considered to be most useful are available as Mineral Colloid No's. 101, etc. corresponding to THIXO-JELs No's, 1, 2, 3 and 4. Such materials have pH's (6% concentration in water) in the range of 8 to 9.4, maximum free moisture contents of about 8% and specific gravities of about 2.6, and for the pulverized grade at least about 85% (and preferably 100%) passes through a 200 mesh U.S. Sieve Series sieve. More preferably, the bentonite is one wherein essentially all the particles (i.e., at least 90% thereof, preferably over 95%) pass through a No. 325 sieve and most preferably all the particles pass through such a sieve. The swelling capacity of the bentonites in water is usually in the range of 3 to 15 ml/gram, and its viscosity, at a 6% concentration in water, is usually from about 8 to 30 centipoises.

In a particular preferred embodiment of the invention, the carrier particles comprise agglomerates of finely divided bentonite, of particle sizes less than No. 200 sieve, agglomerated to particles of sizes essentially in the No's 10–100 sieve range, of a bulk density in the range of 0.7 to 0.9 g./ml. and a moisture content of 8 to 13%. Such agglomerates include about 1 to 5% of a binder or agglomerating agent to assist in maintaining the integrity of the agglomerates until they are added to water, in which it is intended that they disintegrate and disperse. A detailed description of the method of preparation of such agglomerates is set forth in the aforementioned U.S. Ser. No. 366,587, filed Apr. 8, 1982 which is incorporated herein by reference.

Instead of utilizing the THIXO-JEL or Mineral Colloid bentonites one may employ products, such as that sold by American Colloid Company, Industrial Division, as General Purpose Bentonite Powder, 325 mesh, which has a minimum of 95% thereof finer than 325 mesh or 44 microns in diameter (wet particle size) and a minimum of 96% finer than 200 mesh or 74 microns diameter (dry particle size). Such a hydrous aluminum silicate is comprised principally of montmorillonite (90% minimum), with smaller proportions of feldspar, biotite and selenite. A typical analysis, on an "anhydrous" basis, is 63.0% silica, 21.5% alumina, 3.3% of ferric iron (as $Fe_2O_3$), 0.4% of ferrous iron (as FeO), 2.7% of magnesium (as MgO), 2.6% of sodium and potassium (as $Na_2O$), 0.7% of calcium (as CaO), 5.6% of crystal water (as $H_2O$) and 0.7% of trace elements.

Although the western bentonites are preferred it is also possible to utilize other bentonites, such as those which may be made by treating Italian or similar bentonites containing relatively small proportions of exchangeable monovalent metals (sodium and potassium) with alkaline materials, such as sodium carbonate, to increase the cation exchange capacities of such products. It is considered that the $Na_2O$ content of the bentonite should be at least about 0.5%, preferably at least 1% and more preferably at least 2% so that the clay will be satisfactory swelling, with good softening and dispersing properties in aqueous suspension. Preferred swelling betonites of the types described above are sold under the trade names Laviosa and Winkelmann, e.g., Laviosa AGB and Winkelmann G-13.

The silicate, which may be employed as a binder to hold together the finely divided bentonite particles in agglomerated form, is preferably a sodium silicate of $Na_2O:SiO_2$ e.g., 1:2.4. The silicate is water soluble and solutions thereof at concentrations up to about 50%, by weight, may be employed in the preparation of the aforementioned betonite agglomerates, all of such solutions being free flowing, especially at the elevated temperatures to which the silicate solution is preferably heated during the preparation procedure.

The cationic compounds are employed as fabric adhesive agents in the carriers of the invention in an amount of from about 0.2 to about 16%, and preferably from about 1 to 5%, by weight. In the fully-formulated detergent compositions of the invention, the cationic compounds are present in an amount of from about 0.01 to about 10%, more usually from about 0.05 to 2%, and preferably from about 0.1 to 1%, by weight. When the fabric-adhesive agent is comprised exclusively of an anionic or nonionic detergent compound, such detergent is present in the carriers in an amount from about 0.2 to less than 5%, by weight, and preferably from about 1 to below 5%, by weight.

The useful primary, secondary and tertiary amines and their water-soluble salts are generally of the formula $R^1R^2R^3N$, wherein $R^1$ represents an alkyl or alkenyl group containing from about 8 to 22 carbon atoms and $R^2$ and $R^3$ each represent hydrogen or hydrocarbyl groups containing from 1 to 22 carbon atoms, the term "hydrocarbyl group" encompassing alkyl, alkenyl, aryl and alkaryl groups including substituted groups of this type, common substituents being hydroxy and alkoxy groups.

Within the general description of amines given above, specific examples include primary tallow amine, primary coconut amine, secondary tallow methyl amine, tallow dimethyl amine, tritallow amine, primary tallow amine hydrochloride, and primary coconut amine hydrochloride.

The useful diamine and diammonium salts have the general formulas: $R^1R^2NR^5NR^3R^4$; $[R^1R^2NR^5NR^3R^4R^6]^+X^-$; $[R^1R^2R^3NR^5NR^4R^6]^+X^-$; $[R^1R^2R^3NR^5NR^4R^6R^7]^+X^-$; wherein $R^1$, $R^2$, and $R^3$ are as defined above, $R^4$, $R^6$ and $R^7$ have the same definition as $R^2$ and $R^3$, and $R^5$ is an alkylene chain having from 4 to 6 carbon atoms wherein the middle carbon atoms may be linked to each other by an ether oxygen or by a double or triple bond. $X^-$ is an anion, preferably chloride, bromide, sulfate, methyl sulfate or similar anion.

Specific examples of diamines and diamine salts include N-coco-1,3-diaminopropane, N-tallow-1,3-diaminopropane, N-oleyl-1,3-diaminopropane, N-tallow-1,3-diaminopropane dioleate and N-tallow-1,3-diaminopropane diacetate.

Also suitable for use herein are the ethoxylated amine and diamine salts with fatty alkyl groups or coconut, tallow and stearyl and containing from about 2 to 50 moles of ethylene oxide.

The useful quaternary ammonium compounds are generally of the formula $[R^1R^2R^3R^4N]^+X^-$, wherein $R^1$, $R^2$, $R^3$ and X are as defined above, $R^4$ is an organic radical selected from among those defined for $R^1$, $R^2$ and $R^3$. Although not indicated in the above formula, $R^1$ and/or $R^4$ may be attached to the quaternary nitrogen atom through an ether, alkoxy, ester or amide linkage. Among the quaternary ammonium compounds known to add substantivity to fabrics, particularly fabrics containing substantial amounts of cotton, three basic types are particularly useful for the invention: (1) alkyl dimethyl ammonium compounds; (2) amido alkoxylated ammonium compounds; and (3) alkyl amido imidazolinium compounds. A detailed description of these three types of compounds is set forth by R. Egan in *Journal American Oil Chemists' Society,* January, 1978 (vol. 55), pages 118–121, such disclosure being incorporated herein by reference.

Long chain quaternary ammonium compounds are generally preferred for use herein, namely, compounds wherein the number of carbon atoms is greater than eight. Within the more general description provided above concerning quaternary ammonium compounds useful for the invention, preferred specific quaternary ammonium compounds include di-hydrogenated tallow dimethyl ammonium methyl sulfate; di-hydrogenated tallow dimethyl ammonium chloride, and 1-methyl-1-alkylamidoethyl-2-alkylimidazolinium methyl sulfate wherein the "alkyls" are oleyl or saturated hydrocarbyls derived from tallow or hydrogenated tallow. Dimethyl alkyl benzyl quaternaries that are useful include those wherein the alkyl group is of a mixture of alkyls of 10 to 18 carbon atoms or 12 to 16 carbon atoms, e.g., lauryl, myristal and palmityl. The various materials mentioned above are available commercially from various manufacturers, those from Sherex Chemical Company being identified by tradenames such as Adogen; Arosurf: Variquat; and Varisoft.

The quaternary ammonium salts employed herein are preferably substantially free of a conductive salt; the term "conductive salt" being used herein to refer to salts which are electrically conductive in aqueous solution. The conductive salts generally have a cation anion-bond of at least 50% ionic character as calculated in accordance with the method described in Pauling, "The Nature of the Chemical Bond", 3rd Edition, 1960. By use of the term "substantially free" is meant a concentration of conductive salt less than that present at normal impurity levels in the quaternary ammonium compound. Generally, the concentration of conductive salt is below 1%, by weight.

METHOD OF PREPARATION

The perfume-containing carriers of the invention are prepared by methods wherein the carrier particles are initially contacted with the perfume to be employed such that the major portion, preferably substantially all, of such perfume is adsorbed and/or absorbed by such particles. The resulting perfume-containing particles are then contacted with the fabric adhesive agent such that substantially all of such fabric adhesive agent is adsorbed upon the surface of the particles and forms at least a partial coating thereupon.

A preferred technique for contacting the carrier particles with perfume consists of spraying the perfume upon the surface of the particles. This may be effected, for example, by spraying the perfume from a pressurized nozzle so as to produce droplets which contact the surface of the particles, the latter being conveniently on a moving belt, such as, a conveyor belt. Alternatively, the process may be conveniently carried out by spraying the perfume over particles which are contained in a rotary drum or tube inclined at a slight angle, such as, from about 5° to 15°, the rotational speed of such drum or tube being suitably from about 5 to 100 rpm. The range of suitable droplet size for effective spraying may vary from about 10 to about 200 microns in diameter, but preferably should be as small as possible relative to the diameter of the particles being sprayed.

The step of contacting the clay particles with the fabric adhesive agent may be carried out using the same methods described above with regard to perfume sorption upon the carrier particles. Thus, for example, a solution or suspension of an anionic or nonionic detergent compound may be sprayed upon the surface of the particles to form a coating thereon. Where the fabric adhesive agent is a cationic compound, and the carrier particles comprise a clay mineral such as a smectite clay, it is important that the deposition of such compound is effected under conditions which minimize the likelihood of an ion exchange reaction between the clay and the cationic compound. Accordingly, the method of contacting the clay mineral particles with a cationic compound is primarily concerned with avoiding the transformation of a major portion of the clay to a clay complex by an ion exchange reaction, thereby excluding, for example, the methods of preparing a "QA clay" and an "organo-clay complex" referred to in U.S. Pat. Nos. 3,948,790 and 4,292,035, respectively. To promote the adsorption of a cationic compound upon the surface of the clay particles, process conditions which favor swelling of the clay are generally avoided so as to minimize the likelihood of an undesired exchange reaction. Swelling of the clay is particularly favored in an aqueous slurry, hence, the less water which contacts the clay, the less the likelihood of effecting a cation exchange reaction. Accordingly, the weight of aqueous solvent which contacts the clay is generally restricted to an amount less than the weight of the clay, preferably below 50%, and more preferably below 25%, by weight, of such clay.

A preferred method of preparation comprises spraying the surface of the clay particles with a substantially non-aqueous solution or suspension containing the cationic compound, the concentration of water in such solution or suspension being maintained generally below about 50%, by weight, and preferably below about 10%, by weight. This is conveniently effected by spraying the solution or suspension of cationic compounds from a pressurized nozzle as described above. Spraying is preferably carried out at ambient temperatures and generally below 100° F. At temperatures above 100° F., particularly above 140° F., the cationic compounds may be undesirably absorbed into the clay particles. Any organic solvent in which the cationic compound can be dispersed may be conveniently employed to form a solution or suspension for contacting the clay particle. Useful solvents include propylene glycol, hexylene glycol, ethanol and isopropyl alcohol.

In an alternative process of preparation, the particles of clay mineral or zeolite are placed on a vibrating conveyor belt which is continuously wetted with a solution or suspension of a cationic compound, the effect of the vibration being to impart at least a partial coating of the cationic solution or suspension upon the surface of the particles.

In accordance with another embodiment of the invention, finely divided particles as described above are bonded to the surface of a granular detergent composition which is devoid of a soap to form agglomerate particles consisting of detergent-base granules encapsulated within a surface coating of a clay mineral. The agglomerate particles are characterized by an inner portion consisting of the detergent-base granules, and a surface portion contacting and surrounding such inner portion consisting essentially of particles containing at least about 75%, by weight, and preferably greater than about 90%, by weight, of a clay mineral and/or a zeolite and less than about 5%, by weight, of surface active detergent compounds other than cationic detergents, preferably substantially free of such surfactants.

To achieve a substantially continuous external surface of the clay mineral on the agglomerate particle, the carrier particles employed are as small as possible relative to the detergent-base granules, allowing the particles to be closely packed around the granules. The detergent composition granules are preferably spray-dried particles having sizes within mesh Nos. 8 to 100, U.S. Sieve Series. The carrier particles are preferably sufficiently small that they pass through a No. 325 mesh screen, U.S. Sieve Series. The weight ratio of detergent composition granules to clay-containing particles may vary from about 10:1 to about 1:2, preferably from about 5:1 to 1:1. The application of the particles to the base detergent granules may be effected by standard agglomeration techniques and equipment. One method that has been found to be especially useful is to mix the desired weights of the detergent composition granules and finely divided clay powder and while mixing, spray water on to the moving surfaces thereof, or more preferably, spray a dilute sodium silicate solution. Spraying may be carried out at room temperature and should be gradual enough so as to prevent any objectionable lumping of the mixture. Mixing will continue in this manner until the clay particles all adhere to the detergent-base granules, after which mixing may be halted and the product may be screened or otherwise classified to be within the desired product size range. The silicate solution employed is normally at a concentration of about 0.05 to 10%, by weight, typically from about 1 to 6%, by weight. The amount of silicate solution applied to the detergent-base granules generally constitutes from about 0.01 to about 2%, by weight. Satisfactory agglomeration and surface coating are obtained at such concentration using suitable agglomerating equipment, such as an O'Brien agglomerator, or a conventional inclined drum equipped with spray nozzles, baffles, etc. The silicate concentration should not be so high as to inhibit dispersion of the softening particles in the wash solution when the product is employed in laundry operations. Although it is preferred that silicate be employed in the agglomerating spray, useful product is obtainable by utilizing water alone as an agglomerating or binding agent or by employing aqueous solutions of other binders, such as gums, resins and surface active agents.

The sorption of the fabric adhesive agent and perfume upon the surface of the agglomerate particle is carried out using the same methods described above with regard to the preparation of the carriers of the invention. The resulting agglomerate particles are useful laundry products in which the detergent-base granule dissolves and functions in the standard manner in the wash solution while the particles of clay or zeolite become dispersed in the wash solution where they serve as perfume-containing carriers in accordance with the invention.

The laundry detergent compositions with which the present perfume-containing carriers may be incorporated or with which it may be employed may contain one or more surface active agents selected from the group consisting of anionic, nonionic, cationic, ampholytic and zwitterionic detergents. The synthetic organic detergents employed in the practice of the invention may be any of a wide variety of such compounds which are well known and are described at length in the text "Surface Active Agents and Detergents", Vol. II, by Schwartz, Perry and Berch, published in 1958 by Interscience Publishers, the relevant disclosures of which are hereby incorporated by reference.

Among the anionic surface active agents useful in the present invention are those surface active compounds which contain an organic hydrophobic group containing from about 8 to 26 carbon atoms and preferably from about 10 to 18 carbon atoms in the molecular structure and at least one water-solubilizing group selected from the group of sulfonate, sulfate, carboxylate, phosphonate and phosphate so as to form a water-soluble detergent.

Examples of suitable anionic detergents include soaps, such as, the water-soluble salts (e.g., the sodium, potassium, ammonium and alkanol-ammonium salts) of higher fatty acids or resins salts containing from about 8 to 20 carbon atoms and preferably 10 to 18 carbon atoms. Suitable fatty acids can be obtained from oils and waxes of animal or vegetable origin, for example, tallow, grease, coconut oil and mixtures thereof. Particularly useful are the sodium and potassium salts of the fatty acid mixtures derived from coconut oil and tallow, for example, sodium coconut soap and potassium tallow soap.

The anionic class of detergents also includes the water-soluble sulfated and sulfonated detergents having an aliphatic, preferably an alkyl radical containing from about 8 to 26, and preferably from about 12 to 22 carbon atoms. (The term "alkyl" includes the alkyl portion of the higher acyl radicals). Examples of the sulfonated anionic detergents are the higher alkyl mononuclear aromatic sulfonates such as the higher alkyl benzene sulfonates containing from about 10 to 16 carbon atoms in the higher alkyl group in a straight or branched chain, such as, for example, the sodium, potassium and ammonium salts of higher alkyl benzene sulfonates, higher alkyl toluene sulfonates and higher alkyl phenol sulfonates.

Other suitable anionic detergents are the olefin sulfonates including long chain alkene sulfonates, long chain hydroxyalkane sulfonates or mixtures of alkene sulfonates and hydroxyalkane sulfonates. The olefin sulfonate detergents may be prepared in a conventional manner by the reaction of $SO_3$ with long chain olefins containing from about 8 to 25, and preferably from about 12 to 21 carbon atoms, such olefins having the formula $RCH{=}CHR_1$ wherein R is a higher alkyl group of from about 6 to 23 carbons and $R_1$ is an alkyl group containing from about 1 to 17 carbon atoms, or hydrogen to form a mixture of sultones and alkene sulfonic acids which is then treated to convert the sultones to sulfonates. Other examples of sulfate or sulfonate detergents are paraffin sulfonates containing from about 10 to 20 carbon atoms, and preferably from about 15 to 20 carbon atoms. The primary paraffin sulfonates are made by reacting long chain alpha olefins and bisulfites. Paraffin sulfonates having the sulfonate group distributed along the paraffin chain are shown in U.S. Pat. Nos. 2,503,280;

2,507,088; 3,260,741; 3,372,188 and German Pat. No. 735,096.

Other suitable anionic detergents are sulfated ethoxylated higher fatty alcohols of the formula $RO(C_2H_4O)_mSO_3M$, wherein R is a fatty alkyl of from 10 to 18 carbon atoms, m is from 2 to 6 (preferably having a value from about 1/5 to ½ the number of carbon atoms in R) and M is a solubilizing salt-forming cation, such as an alkali metal, ammonium, lower alkylamino or lower alkanolamino, or a higher alkyl benzene sulfonate wherein the higher alkyl is of 10 to 15 carbon atoms. The proportion of ethylene oxide in the polyethoxylated higher alkanol sulfate is preferably 2 to 5 moles of ethylene oxide groups per mole of anionic detergent, with three moles being most preferred, especially when the higher alkanol is of 11 to 15 carbon atoms. To maintain the desired hydrophile-lipophile balance, when the carbon atom content of the alkyl chain is in the lower portion of the 10 to 18 carbon atom range, the ethylene oxide content of the detergent may be reduced to about two moles per mole whereas when the higher alkanol is of 16 to 18 carbon atoms in the higher part of the range, the number of ethylene oxide groups may be increased to 4 or 5 and in some cases to as high as 8 or 9. Similarly, the salt-forming cation may be altered to obtain the best solubility. It may be any suitably solubilizing metal or radical but will most frequently be alkali metal, e.g., sodium, or ammonium. If lower alkylamine or alkanolamine groups are utilized the alkyls and alkanols will usually contain from 1 to 4 carbon atoms and the amines and alkanolamines may be mono-, di- and tri-substituted, as in monoethanolamine, diisopropanolamine and trimethylamine. A preferred polyethoxylated alcohol sulfate detergent is available from Shell Chemical Company and is marketed as Neodol 25-3S.

The most highly preferred water-soluble anionic detergent compounds are the ammonium and substituted ammonium (such as mono, di and tri-ethanolamine), alkali metal (such as, sodium and potassium) and alkaline earth metal (such as, calcium and magnesium) salts of the high alkyl benzene sulfonates, olefin sulfonates and higher alkyl sulfates. Among the abovelisted anionics, the most preferred are the sodium linear alkyl benzene sulfonates (LABS), and especially those wherein the alkyl group is a straight chain alkyl radical of 12 or 13 carbon atoms.

The nonionic synthetic organic detergents are characterized by the presence of an organic hydrophobic group and an organic hydrophilic group and are typically produced by the condensation of an organic aliphatic or alkyl aromatic hydrophobic compound with ethylene oxide (hydrophilic in nature). Practically any hydrophobic compound having a carboxy, hydroxy, amido or amino group with a free hydrogen attached to the nitrogen can be condensed with ethylene oxide or with the polyhydration product thereof, polyethylene glycol, to form a nonionic detergent. The length of the hydrophilic or polyoxyethylene chain can be readily adjusted to achieve the desired balance between the hydrophobic and hydrophilic groups.

The nonionic detergent employed is preferably a poly-lower alkoxylated higher alkanol wherein the alkanol is of 10 to 18 carbon atoms and wherein the number of moles of lower alkylene oxide (of 2 or 3 carbon atoms) is from 3 to 12. Of such materials it is preferred to employ those wherein the higher alkanol is a higher fatty alcohol of 11 to 15 carbon atoms and which contain from 5 to 9 lower alkoxy groups per mole. Preferably, the lower alkoxy is ethoxy but in some instances it may be desirably mixed with propoxy, the latter, if present, usually being a minor (less than 50%) constituent. Examplary of such compounds are those wherein the alkanol is of 12 to 15 carbon atoms and which contain about 7 ethylene oxide groups per mole, e.g., Neodol ®25-7 and Neodol 23-6.5, which products are made by Shell Chemical Company, Inc. The former is a condensation product of a mixture of higher fatty alcohols averaging about 12 to 15 carbon atoms, with about 7 moles of ethylene oxide and the latter is a corresponding mixture wherein the carbon atom content of the higher fatty alcohol is 12 to 13 and the number of ethylene oxide groups per mole averages about 6.5. The higher alcohols are primary alkanols. Other examples of such detergents include Tergitol ®15-S-7 and Tergitol 15-S-9, both of which are linear secondary alcohol ethoxylates made by Union Carbide Corporation. The former is a mixed ethoxylation product of an 11 to 15 carbon atom linear secondary alkanol with seven moles of ethylene oxide and the latter is a similar product but with nine moles of ethylene oxide being reacted. Also useful in the present compositions are the higher molecular weight nonionics, such as Neodol 45-11, which are similar ethylene oxide condensation products of higher fatty alcohols, the higher fatty alcohol being of 14 to 15 carbon atoms and the number of ethylene oxide groups per mole being about 11. Such products are also made by Shell Chemical Company.

Zwitterionic detergents such as the betaines and sulfobetaines having the following formula are also useful:

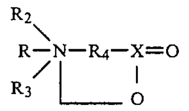

wherein R is an alkyl group containing from about 8 to 18 carbon atoms, $R_2$ and $R_3$ are each an alkyl or hydroxyalkyl group containing about 1 to 4 carbon atoms, $R_4$ is an alkylene or hydroxyalkylene group containing 1 to 4 carbon atoms, and X is C or S:O. The alkyl group can contain one or more intermediate linkages such as amide, ether, or polyether linkages or nonfunctional substituents such as hydroxyl or halogen which do not substantially affect the hydrophobic character of the group. When X is C, the detergent is called a betaine; and when X is S:O, the detergent is called a sulfobetaine or sultaine.

Cationic surface active agents may also be employed. They comprise surface active detergent compounds which contain an organic hydrophobic group which forms part of a cation when the compound is dissolved in water, and an anionic group. Typical cationic surface active agents are amine and quaternary ammonium compounds.

Examples of suitable synthetic cationic detergents include: normal primary amines of the formula $RNH_2$ wherein R is an alkyl group containing from about 12 to 15 atoms; diamines having the formula $RNHC_2H_4NH_2$ wherein R is an alkyl group containing from about 12 to 22 carbon atoms, such as N-2-aminoethyl-stearyl amine and N-2-aminoethyl myristyl amine; amide-linked amines such as those having the formula $R_1CONHC_2H_4NH_2$ wherein $R_1$ is an alkyl group containing about 8 to 20 carbon atoms, such as N-2-amino ethylstearyl amide and N-amino ethylmyristyl amide; quaternary ammonium compounds wherein typically one of the groups linked to the nitrogen atom is an alkyl group containing about 8 to 22 carbon atoms and three of the groups linked to the nitrogen atom are alkyl groups which contain 1 to 3 carbon atoms, including alkyl groups bearing inert substituents, such as phenyl groups, and there is present an anion such as halogen, acetate, methosulfate, etc. The alkyl group may contain intermediate linkages such as amide which do not substantially affect the hydrophobic character of the group, for example, stearyl amido propyl quaternary ammonium chloride. Typical quaternary ammonium detergents are ethyl-dimethyl-stearyl-ammonium chloride, benzyl-dimethyl-stearyl ammonium chloride, trimethyl-stearyl ammonium chloride, trimethyl-cetyl ammonium bromide, dimethyl-ethyl-lauryl ammonium chloride, dimethyl-propyl-myristyl ammonium chloride, and the corresponding methosulfates and acetates.

Ampholytic detergents are also suitable for the invention. Ampholytic detergents are well known in the art and many operable detergents of this class are disclosed by Schwartz, Perry and Berch in the aforementioned "Surface Active Agents and Detergents." Examples of suitable amphoteric detergents include: alkyl betaiminodipropionates, $RN(C_2H_4COOM)_2$; alkyl beta-amino propionates, $RN(H)C_2H_4COOM$; and long chain imidazole derivatives having the general formula:

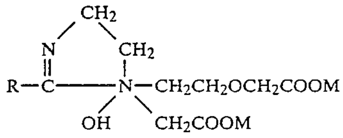

wherein in each of the above formulae R is an acyclic hydrophobic group containing from about 8 to 18 carbon atoms and M is a cation to neutralize the charge of the anion. Specific operable amphoteric detergents include the disodium slat of undecylcycloimidinium-ethoxyethionic acid-2-ethionic acid, dodecyl beta alanine, and the inner salt of 2-trimethylamino lauric acid.

The bleaching detergent compositions of the invention optionally contain a detergent builder of the type commonly used in detergent formulations. Useful builders include any of the conventional inorganic water-soluble builder salts, such as, for example, water-soluble salts of phosphates, pyrophosphates, orthophosphates, polyphosphates, silicates, carbonates, and the like. Organic builders include water-soluble phosphonates, polyphosphonates, polyhydroxysulfonates, polyacetates, carboxylates, polycarboxylates, succinates and the like.

Specific examples of inorganic phosphate builders include sodium and potassium tripolyphosphates, pyrophosphates and hexametaphosphates. The organic polyphosphonates specifically include, for example, the sodium and potassium salts of ethane 1-hydroxy-1,1-diphosphonic acid and the sodium and potassium salts of ethane-1,1,2-triphosphonic acid. Examples of these and other phosphorous builder compounds are disclosed in U.S. Pat. Nos. 3,213,030; 3,422,021; 3,422,137 and 3,400,176. Pentasodium tripolyphosphate and tetrasodium pyrophosphate are especially preferred water-soluble inorganic builders.

Specific examples of non-phosphorous inorganic builders include water-soluble inorganic carbonate, bicarbonate and silicate salts. The alkali metal, for example, sodium and potassium, carbonates, bicarbonates and silicates are particularly useful herein.

Water-soluble organic builders are also useful. For example, the alkali metal, ammonium and substituted ammonium acetates, carboxylates, polycarboxylates and polyhydroxysulfonates are useful builders for the compositions and processes of the invention. Specific examples of acetate and polycarboxylate builders include sodium, potassium, lithium, ammonium and substituted ammonium salts of ethylene diaminetetracetic acid, nitrilotriacetic acid, benzene polycarboxylic (i.e. penta- and tetra-) acids, carboxymethoxysuccinic acid and citric acid.

Water-insoluble builders may also be used, particularly, the complex silicates and more particularly, the complex sodium alumino silicates such as, zeolites, e.g., zeolite 4A, a type of zeolite molecule wherein the univalent cation is sodium and the pore size is about 4 Angstroms. The preparation of such type zeolite is described in U.S. Pat. No. 3,114,603. The zeolites may be amorphous or crystalline and have water of hydration as known in the art.

EXAMPLE 1

Agglomerates of Thixojel No. 1[(1)] clay were used in the present example and are prepared by the procedure described below wherein the following components were used: Thixojel No. 1 clay (325 mesh) and an aqueous agglomerating solution containing 7% of sodium silicate in a ratio of $Na_2O:SiO_2$ of about 1:2.4.

[1]A tradename of a Wyoming bentonite clay sold by Georgia Kaolin Co., Elizabeth, N.J.

The agglomerates were prepared in a rotary drum characterized by a 19.5 inch diameter, a 23.5 inch length and an axis of rotation adjustable between ten and ninety degrees from the vertical.

9.1 kg. of the Thixojel No. 1 clay was charged into the above-described rotary drum which was aligned at an angle of 20 degrees from the vertical. 3.2 kg. of the aqueous silicate solution at a temperature of 43° C. was sprayed on to the clay while the drum was rotating at about 6 rpm. The axis of the rotary drum was then adjusted to an angle of 70 degrees from the vertical and an additional 3.2 kg. of silicate solution was sprayed on to the clay. The resulting wet agglomerates of clay were transferred in 2 kg. portions to an Aeromatic ST-5 (tradename) fluid bed dryer, manufactured by Aeromatic Corp., Summerville, N.J., and dried to approximately 10 wt.% moisture using an air flow rate of about 6,000 liters per minute and an air inlet temperature of 71° C. Drying was effected in about 15 minutes. The dried material was then passed through a Stokes granulater having a 40 mesh screen, the product particle size being between 40–100 mesh. The fines passing through a 100 mesh screen were recycled to the rotary drum.

A spray dried granular unperfumed detergent composition is used as a component of formulations A, B and C described below and has the following composition:

| Component | Weight Percent |
|---|---|
| Sodium tridecyl benzene sulfonate | 15 |
| Sodium tripolyphosphate | 33 |
| Sodium silicate ($1Na_2O:2.4\ SiO_2$) | 7 |
| Sodium carbonate | 5 |
| Borax | 2 |

-continued

| Component | Weight Percent |
|---|---|
| Sodium sulfate | 27.8 |
| Carboxymethyl cellulose | 0.2 |
| moisture | 10 |

Formulation A—100 grams of the above-described unperfumed detergent composition was blended with 0.2 g. of a conventional detergent-type perfume based on limonene, gerantol, citral, cedrol, benzyl acetate, p-t-butyl cyclohexyl acetate and other aromatic ingredients in a Twin-shell blender for ten minutes at a blender speed of about 20 rpm.

Formulation B—80 g. of the unperfumed detergent composition described above is blended with 0.2 g. of the same perfume employed in formulation A in accordance with procedure described above. 19.8 g. of agglomerated Thixojel No. 1 is then added to the blender and mixed with the contents thereof for about 10 minutes at a blender speed of about 20 rpm.

Formulation C—19.8 g. of agglomerated Thixojel No. 1 is blended for about 10 minutes with 0.2 g. of the same perfume used in formulations A and B in the twin-shell blender referred to above. The resulting perfume-containing Thixojel clay is then put into a one-liter laboratory model drum which is rotated by a motor at about 10 rpm. Varisoft 3690(1) is then added

[1]Methyl(1)oleyl amido ethyl(2)oleyl imidazolinium-methyl sulfate (75% active ingredients in 25% isopropanol) manufactured by Sherex Chemical Company, Dublin, Ohio. dropwise to the clay while the drum is rotating so as to simulate in the laboratory-scale equipment the effect of spraying the QA compound upon the clay. The amount of QA compound added to the particules relative to the weight of clay (based on the active ingredient in the Varisoft 3690) is 0.15 g./10 g. clay. The resulting agglomerates of clay are then removed from the rotating drum and mixed for about 10 minutes in a blender with 80 g. of the unperfumed detergent composition described above.

Accordingly, formulation A represents a typical conventional detergent formulation containing perfume; formulation B represents a detergent formulation similar to A but which in addition contains clay agglomerates; and formulation C represents a detergent formulation containing the perfume-containing carrier of the invention.

Perfume tests are carried out using cotton, Dacron polyester, and Dacron polyester/cotton (65/35) swatches and terry towels which are washed in a conventional U.S. washing machine at 25° C. using water having a hardness of 100 ppm as calcium carbonate. Each of three sets of the above-described swatches are separately washed using 100 g. of formulations A, B and C, a different formulation being used for each washing.

When the washing procedure is completed, the swatches are evaluated and the fabrics washed in formulation C are found to retain a stronger perfume fragrance than the fabrics washed in formulations A and B.

Based on the above, the use of the perfume-containing carrier of the invention is a granular detergent composition results in a significant increase in the retention of a perfume fragrance on the laundered fabrics.

EXAMPLE 2

The perfume tests described in Example 1 are repeated using 100 g. of formulations A, B and C for each washing as described in the example except that in formulation C, instead of adding Varisoft 3690 to the perfume-containing Thixogel clay, there is added primary tallow amine.

When the washing procedure is completed, the swatches are evaluated and the fabrics washed in formulation C are found to have a stronger perfume fragrance than the fabrics washed in formulations B and C.

Improved perfume fragrance is achieved when the above-described perfume test is repeated using instead of primary tallow amine, one of the following amines, diamines and diamine salts to coat the Thixogel clay in formulation C: secondary tallow methyl amine, tritallow amine, N-coco-1,3-diaminopropane, N-tallow-1,3-diaminopropane and N-tallow-1,3-diaminopropane diacetate.

What is claimed is:

1. A perfume-containing carrier consisting essentially of (i) discrete particles containing at least 90%, by weight, of a smectite-type clay and/or a zeolite; (ii) a perfume, said perfume being absorbed and/or absorbed on said particles; and (iii) a fabric-adhesive agent comprising at least one of an anionic detergent compound, a nonionic detergent compound, or a cationic compound selected from the group consisting of primary, secondary and tertiary amines and their water-soluble salts, diamine and diammonium salts, and quaternary ammonium, phosphonium and sulfonium compounds, said fabric-adhesive agent being in contact with said particles and forming at least a partial coating upon the surface thereof, the perfume-containing carrier containing less than about 5%, by weight, of surface active detergent compounds other than cationic detergents.

2. A carrier in accordance with claim 1 wherein said fabric adhesive agent is a quaternary ammonium compound.

3. A carrier in accordance with claim 2 wherein the amount of said quaternary ammonium compound is from about 0.2 to 16%, by weight.

4. A carrier in accordance with claim 1 wherein the weight of said fabric adhesive agent is from about 0.2 to less than about 5%, by weight.

5. A carrier in accordance with claim 1 wherein the weight of perfume is from about 0.2 to about 10%, by weight.

6. A carrier in accordance with claim 1 wherein said particles contain a bentonite clay.

7. A particulate laundry detergent composition comprising:

(a) from about 0.1 to about 50%, by weight, of a perfume-containing carrier consisting essentially of (i) discrete particles containing at least 90%, by weight, of a smectite-type clay and/or a zeolite; (ii) a perfume; and (iii) a fabric-adhesive agent comprising at least one of an anionic detergent compound, a nonionic detergent compound, or a cationic compound selected from the group consisting of primary, secondary and tertiary amines and their water-soluble salts, diamine and diammonium salts, and quaternary ammonium, phosphonium and sulfonium compounds, said fabric-adhesive agent being in contact with said particles and forming at least a partial coating upon the surface thereof, the perfume-containing carrier containing less than about 5%, by weight, of detergent compounds other than cationic detergents;

(b) from about 2 to about 50%, by weight, additional to any detergent compound in said carrier, of one or more surface active detergent compounds selected from the group consisting of anionic, nonionic, cationic, ampholytic and zwitterionic detergent compounds;

(c) from about 0 to about 70%, by weight, of a detergent builder salt; and (d) the balance comprising water and optionally a filler salt.

8. A particulate laundry detergent composition in accordance with claim 7 wherein said perfume is adsorbed and/or absorbed on said particles.

9. A particulate laundry detergent composition in accordance with claim 7 which additionally contains a second perfume to supplement the fragrance provided by said perfume-containing carrier.

10. A laundry detergent composition in accordance with claim 1 wherein said detergent builder salt is present in an amount of from about 5 to about 50%, by weight.

11. A laundry detergent composition in accordance with claim 7 wherein said smectite-type clay is a bentonite clay.

12. A laundry detergent composition in accordance with claim 7 wherein the weight ratio of the clay mineral and/or zeolite to perfume in said carrier is from about 10:1 to about 200:1.

13. A laundry detergent composition in accordance with claim 7 wherein the weight of perfume in the carrier is from about 0.2 to about 10%, by weight.

14. A laundry detergent composition in accordance with claim 7 wherein said particles contain a zeolite.

15. A laundry detergent composition in accordance with claim 7 wherein said fabric-adhesive agent is a quaternary ammonium compound.

16. A composition in accordance with claim 17 wherein said quaternary ammonium compound contains more than eight carbon atoms.

17. A composition in accordande with claim 7 wherein the amount of fabric adhesive agent is from about 0.05 to about 2%, by weight, of said detergent composition.

18. A process for depositing perfume on fabrics during laundering which comprises contacting the stained and/or soiled fabrics to be laundered with an aqueous solution or dispersion which contains a perfume-coating carrier consisting essentially of (i) discrete particles containing at least 90%, by weight, of a smectite-type clay and/or a zeolite; (ii) a perfume; and (iii) a fabric-adhesive agent comprising at least one of an anionic detergent compound, a nonionic detergent compound, or a cationic compound selected from the group consisting of primary, secondary and tertiary amines and their water-soluble salts, diamine and diammonium salts, and quaternary ammonium, phosphonium and sulfonium compounds, said fabric-adhesive agent being in contact with said particles and forming at least a partial coating upon the surface thereof, the perfume-containing carrier containing less than about 5%, by weight, of surface active detergent compounds other than cationic detergents.

19. A process in accordance with claim 18 wherein said perfume is absorbed and/or absorbed on said particles.

20. A process in accordance with claim 18 wherein said smectite-type clay is a bentonite clay.

21. A process in accordance with claim 18 wherein said particles contain a zeolite.

22. A process in accordance with claim 18 wherein said aqueous solution or dispersion contains a particulate laundry detergent composition comprising (a) from about 0.1 to about 50%, of said perfume-containing carrier; (b) from about 2 to about 50%, by weight, additional to any detergent in said carrier, of one or more surface active detergent compounds selected from the group consisting of anionic, nonionic, cationic, ampholytic and zwitter-ionic detergent compounds; (c) from about 0 to about 70%, by weight, of a detergent builder salt; and (d) the balance comprising water and optionally a filler salt.

23. A process in accordance with claim 18 wherein the weight of perfume in the carrier is from about 0.2 to about 10%, by weight.

24. A laundry detergent product comprising:

(a) agglomerate particles which contain as individual components thereof (i) particles consisting essentially of at least 90%, by weight, of a smectite-type clay and/or a zeolite; and (ii) granules of a detergent composition devoid of a soap; each of said agglomerate particles being comprised of an inner portion and a surface portion, the inner portion of the agglomerate particle being contigous with and essentially surrounded by the surface portion, said inner portion consisting essentially of said angular detergent composition and said surface portion consisting essentially of said particles;

(b) a perfume, said perfume being absorbed and/or absorbed on the surface portion of said agglomerate particles; and (c) a fabric adhesive agent comprising at least one of an anionic detergent compound, a nonionic detergent compound, or a cationic compound selected from the group consisting of primary, secondary and tertiary amines and their water-soluble salts, diamine and diammonium salts, and quaternary ammonium, phosphonium and sulfonium compounds, said fabric-adhesive agent being in contact with the surface portion of said agglomerate particles and forming at least a partial coating thereupon.

25. A laundry product as in claim 24 wherein said particles of a smectite-type clay and/or a zeolite contain less than about 5%, by weight, of surface active detergent compounds other than cationic detergents.

26. A laundry product as in claim 24 wherein the smectite-type clay is a bentonite clay.

27. A laundry product as in claim 24 wherein said granules of detergent composition contain from about 2 to about 50%, by weight, of a surface active detergent compound selected from the group consisting of anionic, nonionic, cationic, ampholytic and zwitterionic detergent compounds.

28. A laundry product as in claim 24 wherein the weight of perfume in the particles is from about 0.2 to about 10%, by weight.

* * * * *